United States Patent
Sawa

[11] 4,033,966
[45] July 5, 1977

[54] NOVEL BERBINE DERIVATIVES

[75] Inventor: Yoshio Sawa, Nishinomiya, Japan

[73] Assignee: Kanebo, Ltd., Tokyo, Japan

[22] Filed: June 24, 1975

[21] Appl. No.: 589,920

[52] U.S. Cl. .................... 260/286 Q; 424/258
[51] Int. Cl.² ........................ C07D 215/20
[58] Field of Search ............ 260/286 Q, 295 R; 424/258

[56] References Cited

UNITED STATES PATENTS

| | | | |
|---|---|---|---|
| 3,835,140 | 9/1974 | Zee-Cheng et al. | 260/286 Q |
| 3,884,911 | 5/1975 | Shimada et al. | 424/258 |
| 3,910,938 | 10/1975 | Ikekawa et al. | 260/295 A |
| 3,920,665 | 11/1975 | Shimada et al. | 424/258 |

OTHER PUBLICATIONS

Fukuda et al., Chemical Abstracts 73:86087a, (1970).
Yu et al., Chemical Abstracts 67:82289w, (1967).
Sun et al., Chemical Abstracts 63:7062d, (1965).
Shamma et al., J. Am. Chem. Soc., 92:16, Aug. 12, 1970.

*Primary Examiner*—Norman A. Drezin
*Attorney, Agent, or Firm*—Haight & Huard

[57] ABSTRACT

Novel berbine derivatives of the formula:

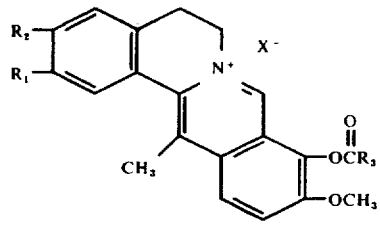

wherein $R_1$ and $R_2$ are each methoxy or jointly a methylenedioxy, $R_3$ is methyl, 4-methoxyphenyl or phenylvinyl, and X is a pharmaceutically acceptable anion. They inhibit the growth of transplanted sarcoma strain in mice.

5 Claims, No Drawings

NOVEL BERBINE DERIVATIVES

This invention relates to novel berbine derivatives of the formula:

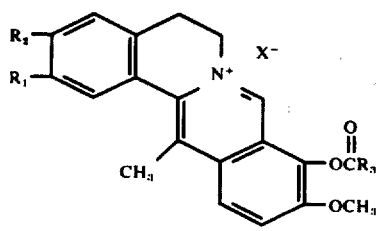

wherein $R_1$ and $R_2$ represent each a methoxy group or jointly a methylenedioxy group, $R_3$ represents a member selected from the group consisting of methyl, 4-methoxyphenyl and phenylvinyl groups, and X represents a pharmaceutically acceptable anion such as a halide, sulfate, phosphate, nitrate and the like.

According to the present invention, it has been found that quarternary ammonium salts of certain acylates of 13-methylberberrubine or 13-methypalmatrubine have a strong inhibitory effect against the growth of transplanted sarcoma strain in mice. They are pharmaceutically acceptable quarternary ammonium salts of acetates, 4-methoxybenzoates and cinnamoates derived from 13-methylberberrubine or 13-methypalmatrubine respectively.

They may be prepared by acylating 13-methyberberrubine or 13-methylpalmatrubine with an appropriate acylating agent in accordance with conventional methods. As the acylating agent, halides, anhydrides or lower alkyl esters such as methyl or ethyl esters of corresonding carboxylic acids may be used. The reaction may be carried out in an inert solvent such as chloroform, ethylenechloride or benzene in the presence or absence of an acid acceptor such as pyridine, quinoline and the like.

The reaction, for example, may be represented by the following reaction scheme:

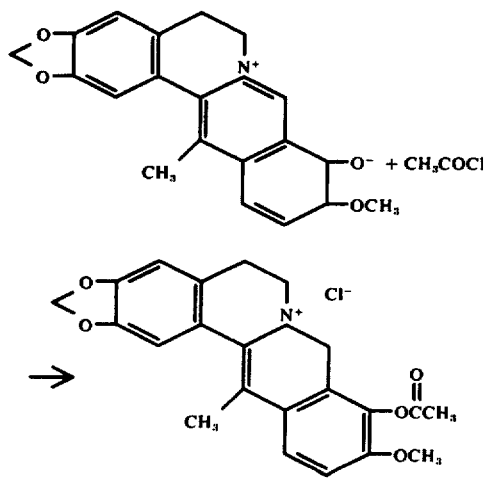

The compounds of the present invention effectively inhibit the growth of transplanted sarcoma strain in mice.

Sarcoma strain S 180(ascitic type) was transplanted into the peritonium of groups of six mice each and test compounds were aministered into mice at a dose of 30mg/kg. of body weight/day for 5 consecutive days. After 1 week, abdominal ascites accumulated was collected and the total packed cell volume (TPCV) was measured. Inhibitory rate of growth of S 180 was calculated by comparing the TPCV between the treated and untreated control groups.

In this test, 13-methylberberrubine acetate chloride and 13-methylberberrubine cinnamoate chloride showed a 100% inhibition respectively.

The following examples will further illustrate the invention.

EXAMPLE 1

3g of 13-methylberberrubine is dissolved in a mixture of 70ml of chloroform and 10ml of pyridine by heating. To the solution is added dropwise a solution of 1.2g of acetyl chloride in 10ml of chloroform. The mixture is refluxed for two hours, and evaporated to one third of the original volume. The resulting crystals are filtered off and recrystallized from methanol.

1.8g of yellow needles of 13-methylberberrubine acetate chloride is obtained. m.p.220°–223° C (with decomposition).

EXAMPLE 2

3g of 13-methylberberrubine is dissolved in a mixture of 70ml of chloroform and 10ml of pyridine by heating. To the solution is added dropwise a solution of 1.1g of anisoyl chloride in 20ml of chloroform. The mixture is refluxed for 2 hours and evaporated to one third of the original volume. The resulting crystals are filtered off and recrystallized from ethanol.

1.7g of yellow needles of 13-methylberberrubine anisoate chloride is obtained. m.p.208°–210° C (with decomposition).

EXAMPLE 3

5g of 13-methylberberrubine is dissolved in a mixture of 100ml of chloroform and 10ml of pyridine by heating. To the solution is added dropwise a solution of 3.2g of cinnamoyl chloride in 30ml of chloroform. The mixture is refluxed for 3 hours and evaporated to one third of the original volume. The resulting crystals are filtered off and recrystallized from ethanol.

3.2g of yellow needles of 13-methylberberrubien cinnamoate chloride is obtained. m.p. 203°–205° C (with decomposition).

EXAMPLE 4

10g of 13-methylpalmatrubine hydrochloride is suspended in 100ml of acetic anhydride. The suspension is heated at 120° C for 3 hours with stirring and then cooled. The resulting crystals are filtered off, washed with cold methanol and then dried.

9.7g of 13-methylpalmatrubine acetate chloride is obtained. m.p.240°–244° C (with decomposition).

Various other examples and modifications of the foregoing examples will be apparent to the person skilled in the art after reading the foregoing specification without departing from the spirit and scope of the invention. All such further examples and modifications are included within the scope of the appended claims.

What is claimed is:

1. A berbine derivative of the formula:

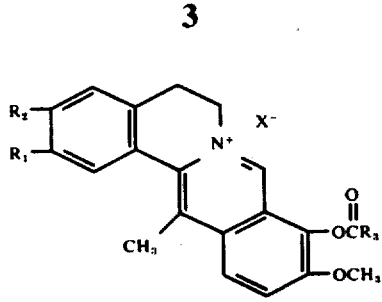

wherein $R_1$ and $R_2$ represent each methoxy or jointly methylenedioxy, $R_3$ represents a member selected from the group consisting of methyl, 4-methoxyphenyl and phenylvinyl, and X represents a pharmaceutically acceptable anion.

2. As a compound of claim 1, 13-methylberberrubine acetate chloride.

3. As compound of claim 1, 13-methylberberrubine anisoate chloride.

4. As a compound of claim 1, 13-methylberberrubine cinnamoate chloride.

5. As a compound of claim 1, 13-methylpalmatrubine acetate chloride.

* * * * *